United States Patent [19]

Mertens et al.

[11] Patent Number: 4,874,756

[45] Date of Patent: Oct. 17, 1989

[54] BENZODIPYRROLES, PROCESSES FOR THE PREPARATION THEREOF AND PHARMACEUTICAL COMPOSITIONS CONTAINING THEM

[75] Inventors: Alfred Mertens, Schriesheim; Wolfgang von der Saal, Weinheim; Herbert Berger, Mannheim; Bernd Müller-Beckmann, Grüstadt; Klaus Strein, Hemsbach, all of Fed. Rep. of Germany

[73] Assignee: Boehringer Mannheim GmbH, Mannheim, Fed. Rep. of Germany

[21] Appl. No.: 902,182

[22] Filed: Aug. 29, 1986

[30] Foreign Application Priority Data

Aug. 29, 1985 [DE] Fed. Rep. of Germany ....... 3530825

[51] Int. Cl.$^4$ .................... A61K 31/55; C07D 487/04
[52] U.S. Cl. .................. 514/212; 514/231.5;
514/232.5; 514/278; 514/316; 514/322;
514/397; 514/409; 514/411; 540/543; 540/602;
544/130; 544/144; 546/15; 546/187; 546/199;
548/336; 548/411; 548/433
[58] Field of Search ..................... 514/411, 212, 231.5,
514/232.5, 278, 316, 322, 397, 409; 548/336,
433; 540/543, 602; 544/130, 144; 546/15, 187,
199

[56] References Cited

U.S. PATENT DOCUMENTS

| | | | |
|---|---|---|---|
| 3,505,353 | 4/1970 | Thomas | 548/433 |
| 3,600,401 | 8/1971 | Thomas | 548/433 |
| 3,959,232 | 5/1976 | Stapler et al. | 528/341 |
| 4,115,404 | 9/1978 | Greenhalgh et al. | 549/299 |
| 4,122,087 | 10/1978 | Greenhalgh et al. | 548/433 |
| 4,650,882 | 3/1987 | Kenyon et al. | 548/433 |
| 4,666,923 | 5/1987 | Hölck et al. | 546/15 |

FOREIGN PATENT DOCUMENTS

| | | |
|---|---|---|
| 216165 | 4/1987 | European Pat. Off. |
| 648639 | 8/1937 | Fed. Rep. of Germany |
| 1795330 | 4/1970 | Fed. Rep. of Germany |
| 2710464 | 9/1977 | Fed. Rep. of Germany |
| 3446417 | 6/1986 | Fed. Rep. of Germany |
| 1251082 | 10/1971 | United Kingdom |

OTHER PUBLICATIONS

G. Lohaus, Chem. Ber. 100, 2719–2729 (1967).
G. Mehta, Synthesis Comm., May 1978, 374–376.
R. Acheson et al., J. C. S. Perkin, 1117–1125 (1978).
Derwent Abstract of Japanese, Patent JP55157579.
Derwent Abstract of Japanese Patent JP 70004053.
H. Auterhoff et al., Arch. Pharmaz. 304/71, 288–296 (1971).

Primary Examiner—Mary E. Ceperley
Attorney, Agent, or Firm—Felfe & Lynch

[57] ABSTRACT

The present invention provides compounds of the general formula

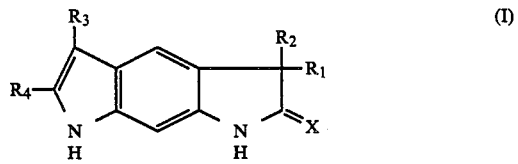

(I)

wherein the variables are as defined herein.

The present invention also provides processes for the preparation thereof, pharmaceutical compositions containing them and intermediates for the preparation thereof.

16 Claims, No Drawings

BENZODIPYRROLES, PROCESSES FOR THE PREPARATION THEREOF AND PHARMACEUTICAL COMPOSITIONS CONTAINING THEM

The present invention is concerned with new benzodipyrroles, processes for the preparation thereof and pharmaceutical compositions containing them.

The new benzodipyrroles according to the present invention are compounds of the general formula:

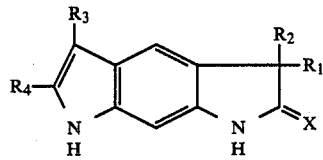

wherein $R_1$ is a hydrogen atom or an alkyl, alkenyl or a cycloalkyl radical; $R_2$ is a hydrogen atom, an alkyl or alkenyl radical, a cyano group, a carbonyl group substituted by hydroxyl, alkyl, alkoxy, amino, alkylamino, dialkylamino or hydrazino or together with $R_1$ represents a cycloalkylene radical or $R_1$ and $R_2$ together form an alkylidene or cycloalkylidene radical; $R_3$ is a hydrogen atom, a cyano group or an alkyl, alkenyl, cycloalkyl, cycloalkenyl, alkylcarbonyl, alkoxycarbonyl, carboxyl, aminocarbonyl, alkylaminocarbonyl, dialkylaminocarbonyl or aryl radical; $R_4$ is a hydrogen atom, an alkyl, trihalogenomethyl, cycloalkyl, hydroxyl, cyano, carboxyl, alkoxycarbonyl, alkylcarbonyl, aminocarbonyl, alkylaminocarbonyl or dialkylaminocarbonyl radical or a heterocyclic five-membered ring with 1 to 4 heteroatoms or a heterocyclic six-membered ring with 1 to 5 heteroatoms, the heteroatoms of the said five- and six-membered rings being the same or different and being nitrogen, oxygen or sulphur and one or more of the nitrogen atoms optionally carries an oxygen atom and the said five- and six-membered rings are optionally substituted by one or more alkyl, alkoxy, alkylthio, hydroxyl, nitro, amino, halogen or cyano groups or $R_4$ is a phenyl ring of the general formula:

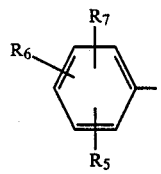

where $R_5$, $R_6$ and $R_7$ are the same or different and each is a hydrogen atom or an alkanesulphonyloxy, trifluoromethanesulphonyloxy, alkanesulphonylamino, trifluoromethanesulphonylamino, N-alkyl-alkanesulphonylamino, N-alkyl-trifluoromethanesulphonylamino, alkylsulphenylmethyl, alkylsulphinylmethyl or alkylsulphonylmethyl radical or a carbonyl group substituted by hydroxyl, alkoxy, amino, alkylamino or dialkylamino or a sulphonyl group substituted by amino, alkylamino, dialkylamino or cyclic imino, whereby a methylene group in the 4-position can be replaced by a sulphur or oxygen atom, or an alkylcarbonylamino, aminocarbonylamino, alkylaminocarbonylamino radical, alkylthio, alkylsulphinyl or aklylsulphonyl radical, a nitro, halogen, amino or hydroxyl group, an alkyl, alkoxy, alkenyloxy, alkynyloxy, cyanoalkoxy, carboxyalkoxy, alkoxycarbonylalkoxy, dialkylamino, 1-imidazolyl, trifluoromethyl or cyano group and X is an oxygen or sulphur atom; the tautomers thereof and the physiologically acceptable salts thereof with inorganic and organic acids.

Since the compounds of general formula (I), when $R_1$ is not a hydrogen atom, possess an asymmetric carbon atom, the present invention also provides the optically active forms and the racemic mixtures of these compounds.

In the case of compounds of general formula (I), in which $R_4$ is a hydroxyl group, the tautomeric forms of the following general formulae are also the subject of the present invention:

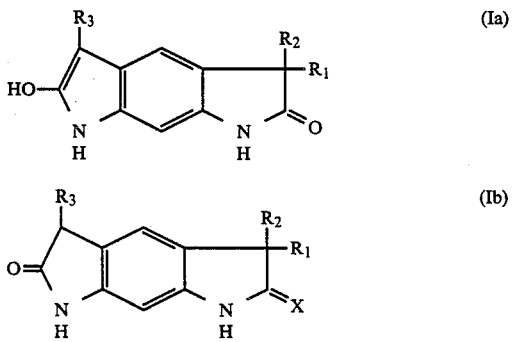

in which $R_1$, $R_2$ and $R_3$ have the same meanings as above.

The new compounds according to the present invention possess valuable pharmacological properties and, in particular, they increase the strength of the heart and/or have a blood pressure lowering action and/or influence the thrombocyte function and improve the microcirculation.

In general formula (I) the substituents $R_1$ and $R_2$ can be the same or different and represent hydrogen, an alkyl, cycloalkyl or alkenyl radical, a cyano group or a carbonyl group substituted by hydroxyl, alkyl, alkoxy, amino, alkylamino, dialkylamino or hydrazino, in which each of the above-mentioned alkyl and alkenyl moieties can be straight-chained or branched and contain 1 to 6 or 2 to 6 carbon atoms, respectively, and the above-mentioned cycloalkyl moiety can contain 3 to 7 carbon atoms.

Preferred in this sense for $R_1$ and $R_2$ are hydrogen, methyl, ethyl, isopropyl, 3-pentyl, allyl, cyclopentyl, cyclohexyl, cyano, acetyl, propionyl, methoxycarbonyl, ethoxycarbonyl, aminocarbonyl, methylaminocarbonyl, dimethylaminocarbonyl and hydrazinocarbonyl.

$R_1$ and $R_2$, together with the carbon atom to which they are attached, can also form a cycloalkylene ring containing 3 to 7 carbon atoms and preferably a spirocyclopropyl, spirocyclobutyl, spirocyclopentyl or spirocyclohexyl radical.

$R_1$ and $R_2$ can together also form an alkylidene or cycloalkylidene radical and preferably an isopropylidene radical.

If $R_3$ is a hydrogen atom or an alkyl, alkenyl, cycloalkyl or cycloalkenyl radical, then it is preferably a hydrogen atom, straight-chained or branched alkyl or alkenyl radical containing 1 to 7 or 2 to 7 carbon atoms, respectively, or a cycloalkyl or cycloalkenyl radical containing 3 to 7 carbon atoms, $R_3$ is preferably a hydrogen atom or a methyl, ethyl, propyl, isopropyl, n-butyl, isobutyl, 3-pentyl, allyl, but-2-enyl, cyclopentyl, cyclohexyl, cyclopentyl or cyclohexyl radical.

If $R_3$ is a cyano group or an alkylcarbonyl, alkoxycarbonyl, aminocarbonyl, alkylaminocarbonyl, dialkylaminocarbonyl or aryl radical, then the above-mentioned alkyl and alkoxy radicals contain up to 7 and preferably up to 5 carbon atoms. Besides cyano, carboxyl or phenyl, $R_3$ is preferably acetyl, propionyl, methoxycarbonyl, ethoxycarbonyl, aminocarbonyl, methylaminocarbonyl or dimethylaminocarbonyl.

If $R_4$ is a hydrogen atom or an alkyl, trihalogenomethyl cycloalkyl, cycloalkenyl, hydroxyl, cyano, carboxyl, alkylcarbonyl, alkoxycarbonyl, alkylaminocarbonyl or dialkylaminocarbonyl radical, then the said alkyl and cycloalkyl radicals contain 1 to 7 and 3 to 7 carbon atoms, respectively. Preferred meanings for $R_4$ include methyl, ethyl, isopropyl, n-butyl, trifluoromethyl, cyclopentyl, cyclohexyl, cyclopentyl, cyclohexenyl, hydroxyl, cyano, carboxyl, acetyl, propionyl, methoxycarbonyl, ethoxycarbonyl, aminocarbonyl, methylaminocarbonyl and dimethylaminocarbonyl.

If $R_4$ is a heterocyclic five-membered ring containing 1 to 4 heteroatoms or a heterocyclic six-membered ring containing 1 to 5 heteroatoms, the heteroatoms in the said five- and six-membered rings being the same or different and being nitrogen, oxygen or sulphur, one or more of the nitrogen atoms optionally carrying oxygen, then preferred radicals include pyrrole, furan, thiophene, pyrazole, imidazole, thiazole, oxazole, triazole, tetrazole, thiadiazole, oxadiazole, pyrazine, N,N-dioxypyrazine, pyrimidine, N,N-dioxypyrimidine, pyridazine, oxazine, thiazine, triazine, tetrazine, pyridyl and N-oxypyridyl.

Alkyl, alkoxy and alkylthio substituents in the heterocyclic five- and six-membered rings can contain up to 6 and preferably up to 4 carbon atoms. Preferred radicals include methyl, ethyl, methoxy, ethoxy, methylthio and ethylthio radicals. Halogen is to be understood to be fluorine, chlorine or bromine, chlorine being preferred.

If $R_4$ means a phenyl ring of general formula (II), then the alkyl moiety of the substituents mentioned in the case of $R_5$, $R_6$ and $R_7$ contains up to 5 and preferably up to 4 carbon atoms. Preferred radicals in this sense include, for example, methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, methylsulphonymethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethylmethanesulphonylamino, N-methyl-ethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-(n-propyl)-aminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-(n-propyl)-aminosulphonyl, N-methylisopropylaminosulphonyl, acetylamino, propionylamino, methylaminocarbonylamino, ethylaminocarbonylamino, propylaminocarbonylamino, methyl, ethyl, propyl, methoxy, ethoxy, propyloxy, allyloxy, but-2-enyloxy, but-3-enyloxy, pent-2-enyloxy, propargyloxy, but-2-ynyloxy, but-3-ynyloxy, cyanomethyloxy, cyanoethyloxy, methoxycarbonylmethyloxy, methoxycarbonylethyloxy, methylthio, ethylthio, methylsulphinyl, ethylsulphinyl, methylsulphonyl and ethylsulphonyl radicals.

In the case of sulphonyl groups which can be substituted by imino groups, the morpholino, pyrrolidino, piperidino and hexamethyleneiminosulphonyl radicals are preferred.

$R_5$ is especially a hydrogen atom or an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by hydroxy, alkoxy, amino, alkylamino or dialkylamino or a sulphonyl group substituted by amino, dialkylamino or morpholino, wherein the alkyl moieties can contain 1 or 2 carbon atoms, or a nitro, cyano or alkylaminosulphonyl radical with 1–4 carbon atoms, an alkylcarbonylamino, aminocarbonylamino or N-alkyl-aminocarbonylamino radical, an alkylthio, alkylsulphinyl or alkylsulphonyl radical, whereby the alkyl moieties can contain 1 or 2 carbon atoms, a halogen, amino, hydroxy, dialkylamino, alkyl, alkoxy, alkenyloxy or alkynyloxy radical preferably with 1–3 carbon atoms, a cyanomethyloxy or methoxycarbonylmethyloxy radical, a trifluoromethyl radical or a 1-imidazolyl radical; $R_6$ is especially a hydrogen atom or an alkyl radical with 1–3 carbon atoms or an alkoxy or dialkylamino radical with 1 or 2 carbon atoms in the alkyl moieties or a halogen atom and $R_7$ is preferably a hydrogen atom or a methoxy radical.

The phenyl radical (II) can contain up to 3 of the above substituents.

Preferred monosubstituted phenyl compounds are the hydroxy, $C_1$–$C_3$ alkyl, $C_1$–$C_3$ alkoxy, allyloxy, propargyloxy, cyanomethyloxy, methoxycarbonylmethyloxy, halogeno, nitro, cyano, aminocarbonyl, methoxycarbonyl, amino, $C_2$–$C_6$ dialkylamino, $C_1$–$C_3$ alkylthio, $C_1$–$C_3$ alkylsulphinyl, $C_1$–$C_3$ alkylsulphonyl, $C_1$–$C_3$ alkylsulphonyloxy and the 1-imidazolyl compounds, the substituent being in the 2-, 3- or 4-position.

Preferred disubstituted compounds contain as substituents alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radicals, a carbonyl group substituted by hydroxy, alkoxy, amino, alkylamino or dialkylamino or a sulphonyl group substituted by amino, dialkylamino or morpholino, an alkylaminosulphonyl, alkylcarbonylamino, aminocarbonylamino or N-alkyl-aminocarbonylamino radical, a hydroxy, alkyl, alkoxy, allyloxy, propargyloxy, cyanomethoxy, methoxycarbonylmethoxy, cyano, halogen, nitro, amino, dialkylamino, alkylthio, alkylsulphinyl, alkylsulphonyl, or 1-imidazolyl group, the two substituents being the same or different and being in the 2,3-, 2,4-, 2,5-, 2,6-, 3,4- or 3,5-position but preferably in the 2,4-2,5- or 3,4-position and the above-mentioned alkyl radicals, alone or in combination with other radicals, can contain up to 3 carbon atoms.

A preferred trisubstituted phenyl radical is the 3,4,5-trimethoxyphenyl radical.

For X, an oxygen or sulphur atom is preferred.

Especially preferred compounds of general formula (I) are those in which $R_1$ and $R_2$ are the same and signify methyl or ethyl radicals or $R_1$ and $R_2$ are different and signify hydrogen atoms or methyl, ethyl, isopropyl, cyclopentyl, cyano, acetyl, methoxycarbonyl, ethoxycarbonyl, aminocarbonyl or hydrazinocarbonyl radicals or $R_1$ and $R_2$ represent a spirocyclopentyl ring when $R_1$ and $R_2$, together with the carbon atom to which they are attached, form a cycloalkyl ring, $R_3$ is hydrogen atom or a methyl, ethyl, isopropyl, n-butyl, allyl, cyclohexyl, cyclopentyl, cyano, ethoxycarbonyl or phenyl radical, $R_4$ is a methyl, ethyl, isopropyl, trifluoromethyl, cyclopentyl, hydroxyl, cyano, acetyl, carboxyl, ethoxycarbonyl, aminocarbonyl, methylaminocarbonyl or dimethylaminocarbonyl radical or $R_4$ is a pyrrole, furan, thiophene, pyrazole, imidazole, thiazole, oxazole, triazole, tetrazole, thiadiazole, oxadiazole, pyridine, N-oxypyridine, pyrazine, N,N-dioxypyrazine, pyrimidine, N,N-dioxypyrimidine, pyridazine, oxazine, thiazine, triazine or tetrazine radical, as well as the methyl, ethyl, methoxy, ethoxy, methylthio, ethylthio and chlorine substituted derivatives thereof, or $R_4$ is a phenyl radical of general formula (II) in which $R_5$ is a hydrogen atom or a methanesulphonyloxy, trifluoromethanesulphonyl, methanesulphonylamino, trifluoromethanesulphonylamino, methanesulphonylmethylamino, trifluoromethanesulphonylmethylamino, methylsulphenylmethyl, methylsulphinylmethyl, methylsulphonylmethyl, aminocarbonyl, aminosulphonyl, methylaminosulphonyl, dimethylaminosulphonyl, acetylamino, methylthio, methylsulphonyl, hydroxyl, methyl, methoxy, propargyloxy, cyanomethoxy, methoxycarbonylmethoxy, cyano, chloro, nitro, amino, dimethylamino, trifluoromethyl or 1-imidazolyl radical, $R_6$ is a hydrogen atom or methyl, methoxy, dimethylamino or chlorine and $R_7$ is a hydrogen atom or a methoxy radical and X is an oxygen atom.

The compounds of general formula (I) can be prepared by methods known from the literature for the synthesis of indoles and oxindoles. In this regard, reference is made to:

(a) P. L. Julian, E. W. Meyer and H. C. Printy, in R. C. Elderfield (ed.), Heterocyclic Compounds, Vol. 1, pp. 1–231, pub. John Wiley & Sons, New York, 1952

(b) R. K. Brown, in W. J. Houlihan (ed.), Heterocyclic Compounds, Vol. 25, part I, pp. 227–537, pub. John Wiley & Sons, New York, 1972.

However, the synthesis routes shown in the following schemes 1, 2 and 3 are especially advantageous.

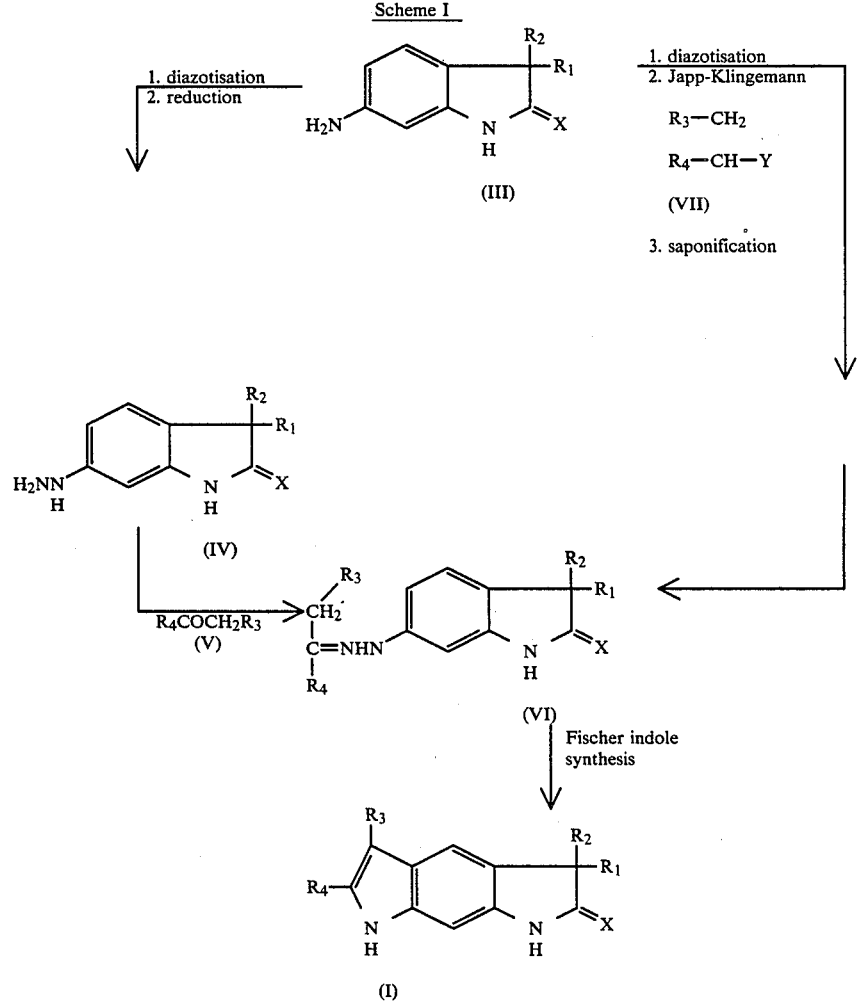

Scheme I

As can be seen from scheme 1, the compounds of general formula (III), which are known from the literature (cf. in this regard Federal Republic of Germany Patent Specifications Nos. P 34 17 643.8 and P 34 46 417.4), in which $R_1$, $R_2$ and X have the above given meanings, can be diazotised and the diazonium salt reduced to a hydrazine (IV). By reaction of the hydrazine with a compound of the general formula:

$$R_4COCH_2R_3 \qquad (V),$$

in which $R_3$ and $R_4$ have the above-given meanings, there is obtained a hydrazone (VI) which can be cyclised by a Fischer indole synthesis to give a compound of general formula (I). On the other hand, a hydrazone of general formula (VI) can also be obtained by reacting a diazonium salt of an amine (III) in a Japp-Klingemann reaction with a compound of general formula (VII), $R_3$ and $R_4$ having the above-given meanings and Y being a residue activating the methine group. This residue can be, for example, an aldehyde, ketone, ester, carboxylic acid or nitrile. The azo compound obtained as intermediate in the reaction mixture is, without isolation, saponified directly to give a hydrazone.

The diazotisation of the amines (III) is preferably carried out under neutral or acidic conditions in a polar solvent, such as water, methanol, ethanol, glacial acetic acid, hydrochloric acid, sulphuric acid or phosphoric acid, at a temperature of from $-70°$ to $+50°$ C. and preferably of from $-5°$ to $+10°$ C. For the diazotisation, there is preferably used an inorganic salt or an organic ester of nitrous acid, for example sodium nitrite, potassium nitrite or amyl nitrite.

The reduction of the diazonium salts is usually carried out in the above-mentioned solvents at a temperature of from $-50°$ C. to the boiling point of the solvent used by preferably at a temperature of from $0°$ to $80°$ C., whereby as reducing agent, there can be used an alkali metal sulphite, sulphur dioxide, a dithionite, stannous chloride, zinc dust, iron, sodium amalgam, triphenylphosphines or an endiol. An electrochemical reduction can also be used.

The reaction of the hydrazines with compounds of general formula (V) can be carried out in a solvent, such as water, alcohol, benzene, toluene, dioxan, dimethylformamide, diethyl ether or tetrahydrofuran, at a temperature of from $-80°$ C. to the boiling point of the solvent used. The addition of an inorganic or organic acid, such as hydrochloric acid, sulphuric acid, phosphoric acid or acetic acid, has also proved to be advantageous.

The Japp-Klingemann reaction is advantageously carried out in the solvents in which the above-described diazotisation can be carried out. Thus, these are especially water, methanol, ethanol, glacial acetic acid, hydrochloric acid, sulphuric acid or phosphoric acid, the temperature used being from $-50°$ C. to $+80°$ C. but preferably from $0°$ to $25°$ C. The following saponification can be carried out thermally or after the addition of an acid or base, for example aqueous sodium or potassium hydroxide solution, hydrochloric acid, sulphuric acid, phosphoric acid or glacial acetic acid, at a temperature up to the boiling point of the solvent.

The Fischer indole synthesis of the hydrazones (VI) is carried out without a solvent or in a solvent, such as alcohol, nitrobenzene, acetic acid, xylene, cumol or toluene, thermally or in the presence of an acidic catalyst which, however, can also be used as solvent, whereby there can be used hydrochloric acid, sulphuric acid, phosphoric acid, polyphosphoric acid, glacial acetic acid, formic acid, zinc chloride, boron trifluoride, a cation exchanger, sulphosalicylic acid or a polyphosphate ester, at a temperature of from $0°$ C. to the boiling point of the solvent used.

The hydrazones (VI) can also be prepared from the amines (III) according to the following scheme 2:

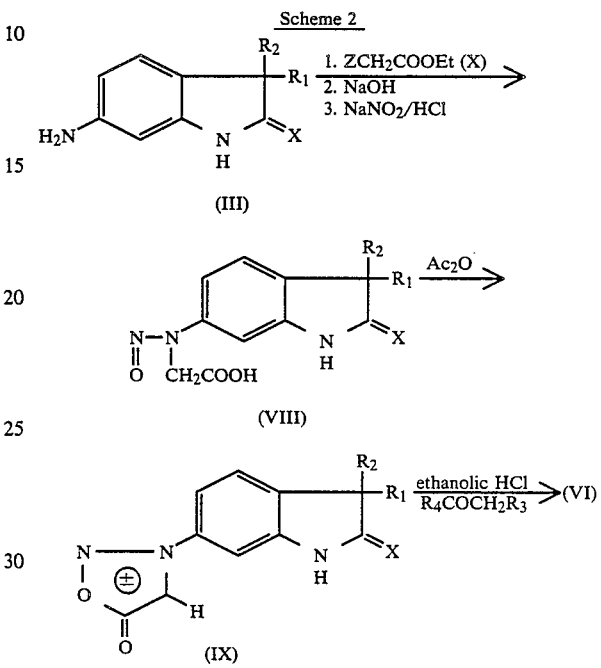

The reaction of compounds (III) with halogenoacetic acid esters (X), in which halogen is fluorine, chlorine, bromine or iodine but is preferably bromine, is advantageously carried out in a polar or non-polar solvent, for example methylene chloride, toluene, dioxan, alcohols or dimethylformamide, at a temperature of from $-50°$ C. and the boiling point of the solvent and preferably at a temperature of from $25°$ to $100°$ C.

The esters so obtained can be saponified according to well-known processes, for example with an inorganic base, such as sodium hydroxide, potassium hydroxide, sodium hydrogen carbonate or potassium hydrogen carbonate, in a protic solvent, such as water or alcohol, or with an inorganic or organic acid, such as hydrochloric acid, sulphuric acid, glacial acetic acid, phosphoric acid or polyphosphoric acid, optionally with the addition of a solvent, such as water or alcohol.

The nitrosation of the acids obtained to give compounds of general formula (VIII) is preferably carried out under neutral to acidic conditions in a polar solvent, such as water, methanol, ethanol, glacial acetic acid, hydrochloric acid, sulphuric acid or phosphoric acid, at a temperature of from $-70°$ to $+50°$ C. and preferably of from $-5°$ to $+10°$ C. The for nitrosation, there is preferably used an inorganic salt or an organic ester or nitrous acid, for example sodium or potassium nitrite or amyl nitrite.

The reaction of the N-nitroso-carboxylic acids (VIII) to give the syndnones (IX) is carried out in an inert solvent, for example dioxan, diethyl ether, tetrahydrofuran or toluene, with a water-removing agent, for example acetic anhydride, propionic acid anhydride, sulphuric acid, phosphoric acid, phosphorus pentachloride or phosphorus trichloride, at a temperature of from −50° C. to the boiling point of the solvent but preferably at a temperature of from 25° to 100° C.

The sydnones (IX) can be decomposed under acidic conditions to give the hydrazines (IV) which can be take up in situ with the ketones (V) to give the hydrazones (VI). As acid for the saponification of the syndones, there can be used an inorganic acid, for example, hydrochloric acid, sulphuric acid, phosphoric acid or polyphosphoric acid, or an organic acid, such as glacial acetic acid, at a temperature of from −70° to +100° C., and preferably of from 0° to 70° C.

Alternatively to schemes 1 and 2, the compounds of general formula (I) can also be prepared by the oxindole synthesis according to the following scheme 3 (cf. P. L. Julian, E. W. Meyer and H. C. Printy in R. C. Elderfield (ed.), Heterocyclic Compounds, Vol. 3, pub. John Wiley & Sons, New York, 1952, pp. 128–142).

Hinsberg synthesis: reaction of aromatic amines with the bisulphite addition compounds of ketones Brunner synthesis: cyclisation of aromatic amines via the hydrazide to the oxindoles Stellé synthesis: cyclisation of aromatic amines via an amide to the oxindole.

ture of from 0° to 60° C., with a per acid, such as performic acid or m-chlorobenzoic acid, in glacial acetic acid, trifluoroacetic acid, methylene chloride or chloroform, at a temperature of from 0° to 60° C.

(b) For the preparation of compounds of general formula (I), in which $R_4$ is a radical of general formula (II) and $R_5$ is an alkylsulphinyl, alkylsulphonyl, alkylsulphinylmethyl or alkylsulphonylmethyl radical, by subsequent oxidation of a compound of the general formula:

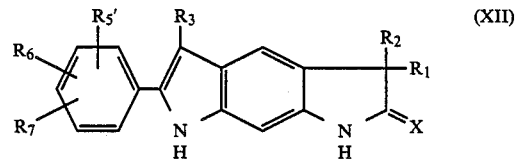

wherein $R_1$, $R_2$, $R_3$, $R_6$, $R_7$ and X have the same meanings as above and $R'_5$ is an alkylthio or alkylsulphenylmethyl radical with, in each case, up to 3 carbon atoms in the alkyl moiety.

The oxidation is preferably carried out in a solvent or solvent mixture, for example in water, water/pyridine,

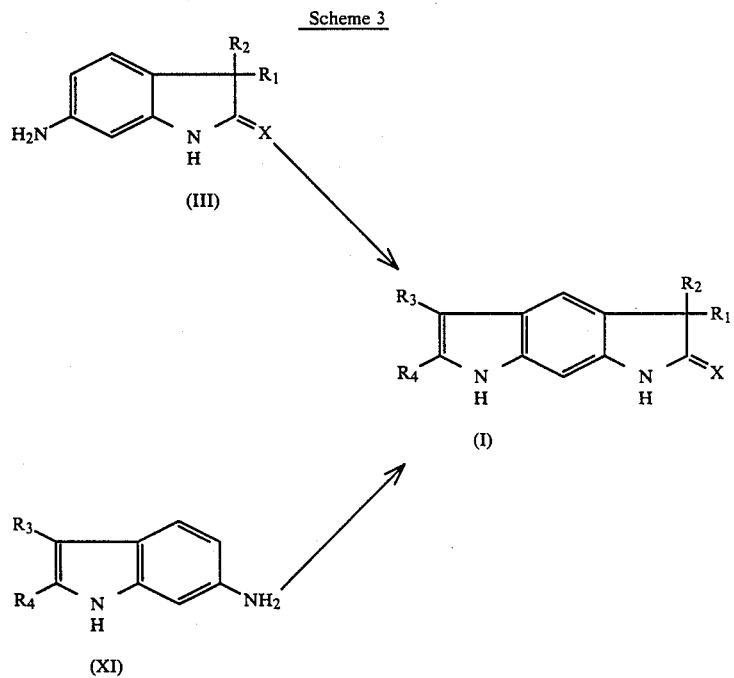

The oxindole synthesis of compounds of general formula (III) to give compounds of general formula (I) only applies to the case in which $R_4$ is a hydroxyl group. Some of the compounds of general formula (XI) are new and these compounds can be prepared by processes known from the literature.

Compounds of general formula (I) can also be subsequently converted into other compounds of general formula (I). This applies, for example:

(a) For the oxidation of a five- or six-membered ring with one or more nitrogen atoms to give the corresponding N-oxides. The oxidation is preferably carried out with one or more equivalents of the oxidation agent used, for example with hydrogen peroxide in glacial acetic acid, trifluoroacetic acid or in formic acid, at a temperature of 20° to 100° C. or in acetone at a temperaacetone, glacial acetic acid, dilute sulphuric acid or trifluoroacetic acid, depending upon the oxidation agent used, preferably at a temperature of from −80° to +100° C.

For the preparation of an alkylsulphinyl or alkylsulphinylmethyl compound of general formula (I), the oxidation is preferably carried out with an equivalent of the oxidation agent used, for example with hydrogen peroxide in glacial acetic acid, trifluoroacetic acid or formic acid, at a temperature of from 0° to 20° C. or in acetone at 0° to 60° C., with a per acid, such as performic acid in glacial acetic acid or trifluoroacetic acid at 0° to 50° C. or with m-chloroperbenzoic acid in methylene chloride or chloroform at −20° to +60° C., with sodium metaperiodate in aqueous methanol or ethanol at −15° to +25° C., with bromine in glacial acetic acid or aqueous acetic acid, with N-bromosuccinimide in ethanol, with tert.-butyl hypochloride in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C., and with sulphuryl chloride in methylene chloride at −70° C., the thioether chlorine complex hereby obtained preferably being hydrolysed with aqueous ethanol.

For the preparation of an alkylsulphonyl or alkylsulphonylmethyl compound of general formula (I), the oxidation is preferably carried out with one or with two equivalents of the oxidation agent used, for example hydrogen peroxide in glacial acetic acid, trifluoroacetic acid or in formic acid, at 20° to 100° C. or in acetone at 0° to 60° C., with a per acid, such as performic acid or m-chloroperbenzoic acid, in glacial acetic acid, trifluoroacetic acid, methylene chloride or chloroform at 0° to 60° C., with nitric acid in glacial acetic acid at 0° to 20° C., with chromic acid or potassium permanganate in glacial acetic acid, water/sulphuric acid or in acetone at 0° to 20° C.

(c) For the preparation of compounds of general formula (I), in which R₄ is a radical of general formula (II) and R₅ is an alkanesulphonyloxy, trifluoromethanesulphonyloxy, alkanesulphonylamino, N-alkylalkanesulphonylamino, trifluoromethanesulphonylamino or N-alkyl-trifluoromethanesulphonylamino radical, by the subsequent reaction of a compound of the general formula:

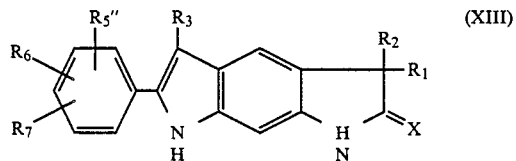

wherein R₁, R₂, R₃, R₆, R₇ and X have the same meanings as above and R″₅ is a hydroxyl or amino group or an N-alkylamino radical with up to 3 carbon atoms in the alkyl moiety, with a sulphonic acid of the general formula:

R₈—SO₂OH     (XIV)

wherein R₈ is an alkyl radical containing up to 3 carbon atoms or a trifluoromethyl radical, in the presence of a water-removing agent and/or a reagent activating the acid or the amine or with reactive derivatives thereof.

The reaction is preferably carried out in a solvent or solvent mixture, such as methylene chloride, diethyl ether, tetrahydrofuran, dioxan or benzene, optionally in the presence of an acid-binding agent, such as sodium carbonate, triethylamine or pyridine, whereby the latter two can simultaneously serve as solvent, in the presence of an acid-activating or water-removing agent, such as thionyl chloride or phosphorus pentachloride, but preferably with a reactive derivative of a compound of general formula (XIV), for example with an anhydride or halide thereof, for example methanesulphonic acid chloride or ethanesulphonic acid chloride, preferably at a temperature of from 0° to 100° C., for example at a temperature of from ambient temperature to 50° C.

(d) For the preparation of compounds of general formula (I), in which R₄ is a radical of general formula (II) and R₂ and/or R₃ is a carbonyl or sulphonyl group substituted by an amino, alkylamino, dialkylamino or hydrazino group, by the subsequent reaction of a compound of the general formula:

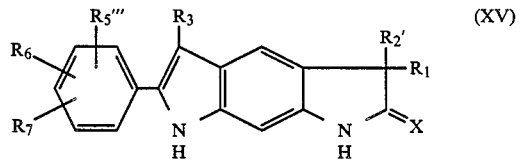

in which R₁, R₃, R₆, R₇ and X have the above-given meanings and R′₂ and/or R‴₅ is a carboxyl or hydroxylsulphonyl group, or a reactive derivative thereof, for example an ester or acid chloride, with hydrazine or an amine of the general formula:

R₉—NH—R₁₀     (XVI)

wherein R₉ and R₁₀ can be the same or different and are hydrogen atoms or alkyl radicals containing up to 5 carbon atoms, or with a reactive derivative thereof if R′₂ and/or R‴₅ represents a carboxyl or hydroxylsulphonyl group.

The reaction is preferably carried out in a solvent or solvent mixture, such as methylene chloride, ethanol, chloroform, carbon tetrachloride, diethyl ether, tetrahydrofuran, dioxan, benzene, toluene, acetonitrile or dimethylformamide, optionally in the presence of an agent activating the acid or removing water, for example in the presence of ethyl chloroformate, thionyl chloride, phosphorus trichloride, phosphorus pentoxide, N,N′-dicyclohexylcarbodiimide/N-hydroxysuccinimide, N,N′-carbonyldiimidazole or N,N′-thionyldiimidazole or triphenylphosphine/carbon tetrachloride, or of an agent activating the hydrazino or amino group, for example phosphorus trichloride, and optionally in the presence of an inorganic base, such as sodium carbonate, or of a tertiary organic base, such as triethylamine or pyridine, which can simultaneously serve as a solvent, at a temperature of from −25° to +250° C. but preferably at a temperature of from −10° C. to the boiling point of the solvent used. Furthermore, water formed during the reaction can be separated off by azeotropic distillation, for example by heating with toluene on a water separator, or by the addition of a drying agent, such as anhydrous magnesium sulphate or of a molecular sieve.

However, the reaction is carried out especially advantageously in an appropriate halide, for example the carboxylic acid sulphonic acid chloride, and hydrazine or an appropriate amine, whereby these can simultaneously sere as solvent, at a temperature of from 0° to 50° C.

(e) For the preparation of compounds of general formula (I), in which R₃ is a cyano group, by the subsequent reaction of a compound of general formula (I), in which R₁, R₂, R₄ and X have the above-given meanings and R₃ is a hydrogen atom, with N-carbonylsulphamoyl chloride, which can also be called chlorosulphonyl isocyanate, in an appropriate solvent according to known processes (Chem. Ber., 100, 2719/1967; Synthesis, 1978, 374 and J. Chem. Soc., Perkin I, 1978, 1117).

The reaction is preferably carried out in a solvent which is inert under the reaction conditions, for example water, methanol, ethanol, n-butanol, dioxan, acetonitrile, nitromethane, pyridine, dimethylformamide or methylene chloride, optionally in the presence of an acid-binding agent.

The reactions are carried out with ice cooling, at ambient temperature or with warming, optionally under a protective gas atmosphere.

(f) For the preparation of compounds of general formula (I), in which $R_3$ and $R_4$ are carboxyl, alkoxycarbonyl or aminocarbonyl groups or $R_4$ is a radical of general formula (II), $R_5$ being a carboxyl, alkoxycarbonyl, aminocarbonyl, alkoxycarbonylalkoxy or carboxyalkoxy radical, by subsequent alcoholysis and/or hydrolysis of compounds of general formula (I), in which $R_3$ and $R_4$ are a cyano group or $R_4$ is a radical of general formula (II), $R_5$ being a cyano or cyanoalkoxy group.

The subsequent alcoholysis and/or hydrolysis is preferably carried out either in the presence of an acid, such as hydrochloric acid, sulphuric acid, phosphoric acid or trichloroacetic acid, or in the presence of a base, such as sodium hydroxide or potassium hydroxide, in an appropriate solvent, such as water, water/methanol, ethanol, water/ethanol, water/isopropanol or water/dioxane, at a temperature of from $-10°$ to $+120°$ C., for example at a temperature between ambient temperature and the boiling point of the reaction mixture.

(g) For the preparation of compounds of general formula (I), in which X is a sulphur atom, by the subsequent introduction of the sulphur atom into compounds of general formula (I), in which $R_1$, $R_2$, $R_3$ and $R_4$ have the above-given meanings and X is an oxygen atom.

The reaction is carried out with reagents known from the literature which transfer the sulphur atom, for example with phosphorus pentasulphide, it being preferable to use 1 to 5 moles but more preferably 1 mold of phosphorus pentasulphide in an appropriate solvent. The solvent can be, for example, tetrahydrofuran, dioxan, benzene, toluene or pyridine, the reaction temperature being from 25° to 125° C.

However, it is preferred to use pyridine with a reaction period of from 1 to 10 hours and preferably of 5 hours, depending upon the reaction components.

Furthermore, the compounds obtained of general formula (I) can, if desired, be subsequently converted into their physiologically acceptable acid-addition salts with organic and inorganic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned hereinbefore, the new compounds of general formula(I), the tautomers thereof and the physiologically acceptable acid-addition salts thereof possess, with a long period of action, superior pharmacological properties, especially a blood pressure lowering and/or positive inotropic action and/or influence the thrombocyte function and improve the microcirculation.

For the preparation of pharmaceutical compositions, the compounds of general formula (I) are mixed in known manner with appropriate pharmaceutical carrier substances and formed, for example, into tablets or dragees or, with the addition of appropriate adjuvants, are suspended or dissolved in water or an oil, for example olive oil.

The new compounds according to the present invention of general formula (I) and the salts thereof can be administered enterally or parenterally in liquid or solid form. As injection medium it is preferred to use water which contains the additives usual in the case of injection solutions, such as stabilising agents, solubilising agents or buffers.

Additives of this type include, for example, tartrate and citrate buffers, ethanol, complex formers (such as ethylenediamine-tetraacetic acid and the nontoxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in amounts of from 10 to 500 mg. per day, referred to a body weight of 75 kg. It is preferred to administer 1 to 2 tablets with an active material content of 5 to 200 mg. two or three times a day. The tablets can also be retarded in which case only 1 or 2 tablets with 10 to 500 mg. of active material have to be given once per day. The active material can also be administered by injection 1 to 8 times a day or by continuous infusion, in which case amounts of 5 to 200 mg./day normally suffice.

Preferred compounds according to the present invention, apart from the compounds described in the Examples, include the following and the tautomers thereof:

3,3-dimethyl-6-(pyrrol-2-yl)-benzo[1,2-b:5,4-b']dipyrrol-2-(1H, 3H, 7H)-one 3,3-dimethyl-6-(thiazol-4-yl)-benzo[1,2-b:5,4-b']dipyrrol-2-(1H, 3H, 7H)-one 3,3-dimethyl-6-(1,2,4-triazol-3-yl)-benzo[1,2-b:5,4-b']dipyrrol-2-(1H, 3H, 7H)-one 3,3-dimethyl-6-(5-carboxy-1,2,3-triazol-4-yl)-benzo[1,2-b:5,4-b']dipyrrol(1H, 3H, 7H)-one 3,3-dimethyl-6-(5-methylthio-1,3,4-oxadiazol-2-yl)-benzo[1,2-b:5,4-b']dipyrrol-2-(1H, 3H, 7H)-one 3,3-dimethyl-6-(1,2,5-thiadiazol-3-yl)-benzo[1,2-b:5,4-b']dipyrrol-2-(1H, 3H, 7H)-one 3,3-dimethyl-6-(pyrimidin-5-yl)-benzo[1,2-b:5,4-b']dipyrrol-2-(1H, 3H, 7H)-one 3,3-dimethyl-6-(pyrazin-2-yl)-benzo[1,2-b:5,4-b']dipyrrol-2-(1H, 3H, 7H)-one 3,3-dimethyl-6-(N-oxy-4-pyridyl)-benzo[1,2-b:5,4-b']dipyrrol-2-(1H, 3H, 7H)-one 3,3-dimethyl-6-(4-nitrophenyl)-benzo[1,2-b:5,4-b']dipyrrol-2-(1H, 3H, 7H)-one 3,3-dimethyl-6-(4-methylthiophenyl)-benzo[1,2-b:5,4-b']dipyrrol-2-(1H, 3H, 7H)-one 3,3-dimethyl-6-(4-amino-phenyl)-benzo[1,2-b:5,4-b']dipyrrol-2-(1H, 3H, 7H)-one 3,3-dimethyl-6-(4-methylsulphenyl-2-methoxyphenyl)-benzo[1,2-b:5,4-b']dipyrrol-2-(1H, 3H, 7H)-one 3,3-dimethyl-6-(4-methylsulphinyl-2-methoxyphenyl)-benzo[1,2-b:5,4-b']dipyrrol-2-(1H, 3H, 7H)-one 3,3-dimethyl-6-(4-methylsulphonyl-2-methoxyphenyl)-benzo[1,2-b:5,4']dipyrrol-2-(1H, 3H, 7H)-one 3,3-dimethyl-6-(4-methylsulphonyloxy-2-methoxyphenyl)-benzo[1,2-b:5,4-b']dipyrrol-2-(1H, 3H, 7H)-one 3,3,5,6-tetramethylbenzo[1,2-b:5,4-b']dipyrrol-2-(1H, 3H, 7H)-one 3,3,5-trimethylbenzo[12-b:5,4-b']dipyrrol-2-(1H, 3H, 7H)-one 3,3,6-trimethyl-5-cyanobenzo[1,2-b:5,4-b']dipyrrol-2-(1H, 3H, 7H)-one 3,3,6-trimethyl-5-aminocarbonylbenzo[1,2-b:5,4-b']dipyrrol-2-(1H, 3H, 7H)-one 3,3,6-trimethyl-5-ethoxycarbonylbenzo[1,2-b:5,4-b']dipyrrol-2-(1H, 3H, 7H)-one 3,3-dimethyl-6-trifluoromethylbenzo[1,2-b:5,4-b']dipyrrol-2-(1H, 3H, 7H)-one 3,3-dimethyl-6-(cyclohexen-1-yl)-benzo[1,2-b:5,4-b']dipyrrol-2-(1H, 3H, 7H)-one 3,3-dimethyl-6-cyclopropylbenzo[1,2-b:5,4-b']dipyrrol-2-(1H, 3H, 7H)-one 3,3-dimethyl-6-cyanobenzo[1,2-b:5,4-b']dipyrrol-2-(1H, 3H, 7H)-one 3,3-dimethyl-6-acetylbenzo[1,2-b:5,4-b']dipyrrol-2-(1H, 3H, 7H)-one 3,3-dimethyl-5,6-diphenylbenzo[1,2-b:5,4-b']dipyrrol-2-(1H, 3H, 7H)-one 3,3-dimethyl-6-(3,4,5-trimethoxyphenyl)-benzo[1,2-b:5,4-b']dipyrrol-2-(1H, 3H, 7H)-one 3,3-diethyl-6-(4-dimethylaminophenyl)-benzo-1,2-b:5,4-b']dipyrrol-2-(1H, 3H, 7H)-one 3,3-diethyl-6-(2-hydroxy-5-pyrimidinyl)-benzo[1,2-b:5,4-b']dipyrrol-2-(1H, 3H, 7H)-one 3,3-diethyl-6-(4-pyrimidinyl)-benzo[1,2-b:5,4-b']dipyrrol-2-(1H, 3H, 7H)-one 3,3-diethyl-6-(3-hydroxy-6-pyridazinyl)-benzo[1,2-b:5,4-b']dipyrrol-2-(1H, 3H, 7H)-one 6'-(2-methyl-4-oxazolyl)-spiro[cyclopentan-2,3'-benzo[1',2'-b:5',4'-b]dipyrrol]-2'-(1H', 3'H, 7'H)-one 6'-(2-chloro-4-pyridyl)-spiro[cyclopentan-1,3'-benzo[1',2'-b:5',4'-b']dipyrrol]-2'-(1'H, 3'H, 7'H)-one 6'-(2-methyl-4-pyridyl)-spiro[cyclopentan-1,3'-benzo[1',2'-b:5',4'-b']dipyrrol]-2'-(1'H, 3'H, 7'H)-one 3-isopropyliden-6-(2-pyridyl)-benzo[1,2-b:5,4-b']dipyrrol-2-(1H, 3H, 7H)-one 3-methyl-3-ethoxycarbonyl-5-methyl-6-phenylbenzo[1,2-b:5,4-b']dipyrrol-2-(1H, 3H, 7H)-one 3-methyl-3-ethoxycarbonyl-6-(4-trifluoromethylsulphonyl-2-methoxyphenl)-benzo[1,2-b:5,4-b']dipyrrol-2-(1H, 3H, 7H)-one 2-methoxyphenyl)-benzo[1,2-b:5,4-b']dpyrrol-2-(1H, 3H, 7H)-one 3-methyl-3-ethoxycarbonyl-6-(4-morpholinylsulphonyl-2-methoxyphenyl)-benzo[1,2-b:5,4-b']dipyrrol-2-(1H, 3H, 7H)-one 3-methyl-6-(2-furanyl)-benzo[1,2-b:5,4-b']dipyrrol-2-(1H, 3H, 7H)-one 3-methyl-6-(imidazol-4-yl)-benzo[1,2-b:5,4-b']dipyrrol-2-(1H, 3H, 7H)-one 3-methyl-6-(2,4-dimethoxyphenyl)-benzo[1,2-b:5,4-b']dipyrrol-2-(1H, 3H, 7H)-one 3-methyl-6-(2-methoxy-4-aminosulphonylphenyl)-benzo[1,2-b:5,4-b']dipyrrol-2-(1H, 3H, 7H)-one 3-methyl-6-(2-methoxy-4-methylsulphonylaminophenyl)-benzo[1,2-b:5,4-b']dipyrrol-2-(1H, 3H, 7H)-one 3-methyl-6-(2-methoxy-4-methylsulphenymethylphenyl)-benzo[1,2-b:5,4-b']dipyrrol-2-(1H, 3H, 7H)-one 3-methyl-6-(2-methoxy-4-methylsulphinylmethylphenyl)-benzo[1,2-b:5,4-b']dipyrrol-2-(1H, 3H, 7H)-one 3-methyl-6-(2-methoxy-4-methylsulphonylmethylphenyl)-benzo[1,2-b:5,4-b']dipyrrol-2-(1H, 3H, 7H)-one 3-ethyl-6-(2-methoxy-4-cyanomethyloxyphenyl)-benzo[1,2-b:5,4-b']dipyrrol-2-(1H, 3H, 7H)-one 3-ethyl-6-(2-methoxy-4-propargyloxyphenyl)-benzo[1,2-b:5,4-b']dipyrrol-2-(1H, 3H, 7H)-one 3-ethyl-6-(4-pyridyl)-benzo[1,2-b:5,4-b']dipyrrol-2-(1H, 3H, 7H)-one 7-cyclopentyl-6-(4-pyridyl)-benzo[1,2-b:5,4-b']dipyrrol-2-(1H, 3H, 7H)-one 3,3,5-trimethylbenzo[1,2-b:5,4-b']dipyrrol-2,6-(1H, 3H, 5H, 7H)-dione.

The following Examples are given for the purpose of illustrating the present invention:

EXAMPLE 1

3,3-Dimethyl-6-(4-pyridyl)-benzo[1,2-b:5,4-b']dipyrrol-2-(1H, 3H, 7H)-one (a) 6.8 g. (38 mmole) 6-amino-3,3-dimethylindolin-2-one are dissolved in 125 ml. 50% sulphuric acid and 2.8 g. (40.6 mmole) sodium nitrite, dissolved in 25 ml. water, added dropwise thereto at a temperature below 5° C. After 15 minutes, 0.5 g. urea is added thereto and stirring continued for 15 minutes. 26.35 g. (116.8 mmole) Stannous chloride dihydrate, dissolved in 20 ml. concentrated hydrochloric acid, are added dropwise thereto at 5° C. After 2 hours, the solution is mixed with 6.9 g. (57 mmole) 4-acetylpyridine, stirred for 2 hours at 25° C., the residue is filtered off with suction, suspended in water, neutralised with aqueous ammonia solution and filtered off with suction. There are obtained 8.5 g. (76% are theory) 4-acetylpyridine(3,3-dimethyl-2-oxoindoline-6-hydrazone); m.p. 272°–274° C.

(b) 8.3 g. (28.2 mmole) of the hydrazone thus obtained are stirred with 50 ml. polyphosphoric acid under an atmosphere of nitrogen for 6 hours at an oil bath temperature of 110°–120° C. The cooled reaction mixture is worked up with ice water and the suspension is neutralised with concentrated aqueous ammonia solution and filtered off with suction. The residue is recrystallised from methanol/methylene chloride. There are obtained 5.18 g. (66% of theory) of the title compound; m.p. >300° C.

The following compounds are obtained analogously to Example 1:

| designation | yield (%) | m.p. °C. (solvent) |
|---|---|---|
| Example 1.1 | | |
| 3,3-dimethyl-6-(3-pyridyl)-benzo-[1,2-b:5,4-b']dipyrrol-2-(1H,3H, 7H)-one × 1 mole methanol from 3-acetylpyridin-(3,3-dimethyl-2-oxoindolin-6-hydrazone) as crude product | 24 | 305 methanol |
| Example 1.2 | | |
| 3,3-dimethyl-6-(pyridazin-4-yl)-benzo[1,2-b:5,4-b']dipyrrol-2-(1H,3H,7H)-one × 1 mole methanol from 4-acetyl-pyridazin-(3,3-dimethyl-2-oxoindolin-6-hydrazone); m.p. 240° C. | 33 | 330 methanol |
| Example 1.3 | | |
| 3,3-dimethyl-6-[4-(1H—imidazol-1-yl)-phenyl]-benzo[1,2-b: 5,4-b']dipyrrol-2-(1H,3H,7H)-one from 4-(1H—imidazol-1-yl)-acetophenone-(3,3-dimethyl-2-oxoindolin-6-hydrazone) as crude product | 23 | >340 methanol |
| Example 1.4 | | |
| 3-methyl-6-(4-pyridyl)-benzo- | 7.5 | >330 |

-continued

| designation | yield (%) | m.p. °C. (solvent) |
|---|---|---|
| [1,2-b:5,4-b']dipyrrol-2-(1H, 3H,7H)-one from 4-acetylpyridin-(3-methyl-2-oxoindolin-6-hydrazone); m.p. 267–270° C. Example 1.5 | | methanol |
| 3-methyl-6-(3-pyridyl)-benzo-[1,2-b:5,4-b']dipyrrol-2-(1H, 3H,7H)-one from 3-acetylpyridine-(3-methyl-2-oxoindoline-6-hydrazone) as crude product | 14 | 330–31 |

EXAMPLE 2

3,3-Dimethyl-6-(4-cyanophenyl)-benzo[1,2-b:5,4-b']dipyrrol-2-(1H, 3H, 7H)-one×1.5 dichloromethane.

The title compound is obtained analogously to Example 1 from 4.4 g. (13.8 mmole) 4-cyanoacetophenone(3,3-dimethyl2-2-oxoindoline-6-hydrazone) (m.p. 242° C.). The purification of the 3.7 g. of crude product obtained is carried out by column chromatography over silica gel (elution agent: methylene chloride/methanol 95:5 v/v). Yield 0.25 g. (6% of theory); m.p. >310° C.

The following compounds are obtained analogously to Example 2:

| designation | yield (%) | m.p. °C. (solvent) |
|---|---|---|
| Example 2.1 3,3,6-trimethylbenzo[1,2-b:5,4-b']dipyrrol-2-(1H,3H,7H)-one from acetone-(3,3-dimethyl-2-oxoindoline-6-hydrazone); m.p. 150° C. | 12.5 | 255 methanol |
| Example 2.2 3,3,5-trimethyl-6-(4-pyridyl)-benzo[1,2-b:5,4-b']dipyrrol-2-(1H,3H,7H)-one from 4-propionylpyridine-(3,3-dimethyl-2-oxoindoline-6-hydrazone); m.p. > 300° C. | 17.9 | >300 methanol |

EXAMPLE 3

3,3-Dimethyl-6-(2-thienyl)-benzo[1,2-b:5,4-b']-dipyrrol-2-(1H, 3H, 7H)-one

Analogously to Example 1, 6.8 g. (38 mmole) 6-amino-3,3-dimethylindolin-2-one are diazotised and reduced. Into the solution are added dropwise 10.9 g. (85 mmole) 2-acetylthiophene and the oil which separates out is taken up in methylene chloride, dried and evaporated. As crude product, there are obtained 11.2 g. 2-acetylthiophene-(3,3-dimethyl-2-oxoindoline-6-hydrazone) which is further reacted without purification.

11 g. of the residue are treated with 50 g. polyphosphoric acid analogously to Example 1. Purification takes place by column chromatography (elution agent: methylene chloride/ethyl acetate 5:1 v/v). Yield 0.6 g. (5.6% of theory); m.p. 265°–270° C., after recrystallisation from ethanol.

EXAMPLE 4

3,3-Dimethyl-6-phenylbenzo[1,2-b:5,4-b']dipyrrol-2-(1H, 3H, 7H)-one×0.5 mole water×0.14 mole ethyl acetate 3.06 g. (17.4 mmole) 6-Amino-3,3-dimethylindoline-2-one are diazotised and reduced analogously to Example 1. Into the solution is added dropwise 0.6 g. (5 mmole) acetophenone and the reaction mixture further stirred for 3 hours at 25° C. The oil which separates out is separated off, worked up with water and subsequently boiled with heptane. The crude product obtained, acetophenone-(3,3-dimethyl-2-oxoindoline-6-hydrazone), is, without further purification, cyclised according to Example 1 and purified according to Example 2 over silica gel (elution agent: ethyl acetate). There is obtained 0.16 g. (11.6% of theory, referred to the amount of acetophenone used) of the title compound; m.p. 270°–273° C.

The following compounds are obtained in a manner analogously to that described in Example 4;

| designation | yield (%) | m.p. °C. |
|---|---|---|
| Example 4.1 3,3-dimethyl-6-(4-methoxyphenyl)-benzo[1,2-b:5,4-b']-dipyrrol-2-(1H,3H,7H)-one × 0.75 mole water from 4-methoxyacetophenone-(3,3-dimethyl-2-oxoindoline-6-hydrazone) | 3 | 273–276 |
| Example 4.2 3,3-dimethyl-6-(4-methylphenyl)-benzo[1,2-b:5,4-b']-dipyrrol-2-(1H,3H,7H)-one × 0.5 mole water × 0.17 mole ethyl acetate from 4-methylacetophenone-(3,3-dimethyl-2-oxoindoline-6-hydrazone) | 8.6 | 278–281 |
| Example 4.3 3,3-dimethyl-6-(4-chlorophenyl)-benzo[1,2-b:5,4-b']dipyrrol-2-(1H,3H,7H)-one × 1.5 mole water × 0.2 mole ethyl acetate from 4-chloroacetophenon-(3,3-dimethyl-2-oxoindoline-6-hydrazone | 5.2 | 261–263 |
| Example 4.4 3,3-dimethyl-6-(2-hydroxyphenyl)-benzo[1,2-b:5,4-b']dipyrrol-2-(1H,3H,7H)-one from 2-hydroxyacetophenone-(3,3-dimethyl-2-oxoindoline-6-hydrazone | 0.3 | 250–255 |

EXAMPLE 5

3,3-Diethyl-6-ethoxycarbonylbenzo[1,2-b:5,4-b']dipyrrol-2-(1H, 3H, 7H)-one 6 g. (34 mmole) 6-amino-3,3-dimethylindolin-2-one are dissolved in 160 ml. 2N hydrochloric acid and 2.51 g. (36.4 mmole) sodium nitrite, dissolved in 20 ml. water, added dropwise thereto at a temperature below 0° C. After 15 minutes, at the same temperature, 23.59 g. (104 mmole) stannous chloride dihydrate, dissolved in 70 ml. 2N hydrochloric acid, are added dropwise thereto. After 30 minutes, the solution is mixed at 0° C. with 5.58 g. (48 mmole) ethyl pyruvate and further stirred for 3 hours at 25° C. The residue obtained is filtered off with suction, again suspended in water and neutralised with aqueous ammonia solution and filtered off with suction. There are obtained, as crude product, 11.2 g. ethyl pyruvate-(3,3-dimethyl2-oxoindoline-6-hydrazone) (m.p. 284°–290° C.) which is further reacted without purification.

11.3 g. of the above crude product are cyclised in polyphosphoric acid analogously to Example 1. Purification is carried out by column chromatography on silica gel (elution agent: methylene chloride/ethanol 95:5 v/v). Yield 0.45 g. (referred to the amount of amine used); m.p. 313°–315° C. after recrystallisation from ethanol.

EXAMPLE 6

3,3-Dimethyl-6-carboxybenzo[1,2-b:5,4-b']dipyrrol-2-(1H, 3H, 7H)-one × 1 mole ethanol 0.5 g (1.8 mmole) of the ester obtained in Example 5 is stirred in 5 ml. 2N aqueous sodium hydroxide solution and 2.5 ml. ethanol for 1 hour at 60° C. The ethanol is subsequently distilled off and the remaining solution is treated with charcoal and acidified with 2N hydrochloric acid. The residue is recrystallised from ethanol/methylene chloride. Yield: 82%; m.p. 304° C.

EXAMPLE 7

3,3-Dimethyl-6-aminocarbonylbenzo[1,2-b:5,4-b']dipyrrol-2-(1H, 3H, 7H)-one × 0.3 mole ethanol 1.6 g. (6.55 mmole) of the carboxylic acid obtained in Example 6 are stirred for 3 hours with 16 ml. thionyl chloride at 60° C. Excess thionyl chloride is subsequently distilled off and the residue is mixed, while cooling, with 20 ml. concentrated aqueous ammonia solution. After 24 hours at 25° C., the precipitate is filtered off with suction and recrystallised from ethanol. Yield 0.18 g. (11% of theory); m.p. 294°–296° C.

EXAMPLE 8

3,3-Dimethylbenzo[1,2-b:6,5,4-b']dipyrrol-2,6-(1H, 3H, 5H, 7H)-dione × 0.5 mole isopropanol × 0.75 mole water (a) 5.0 g. (27 mmole) 6-aminooxoindole (Helv. Chim. Acta, 20, 373/1937) are suspended in 80 ml. dichloromethane, mixed with 6.45 g. (63 mmole) triethylamine and 6.8 g (29 mmole) α-bromoisobutyric acid bromide added dropwise thereto at 5° C. After stirring for 3 hours at 25° C., the solvent is distilled off and the residue is worked up with water and filtered off with suction. There are obtained 4.2 g. (52.4% of theory) α-bromo-N-(2-oxoindolin-6-yl)-isobutyric acid amide; m.p. 211°–212° C.

(b) 3.2 g. (10.8 mmole) of the above amide are well mixed with 7.1 g. aluminium trichloride and heated for 5 hours, while stirring, to 160° C. The cooled residue is worked up with water and a little 2N hydrochloric acid and filtered off with suction. The precipitate is purified over silica gel (elution agent: methylene chloride/methanol 96:4 v/v). Yield 0.27 g. (11.7% of theory); m.p. 280°–282° C., after recrystallisation from isopropanol.

EXAMPLE 9

6'-(4-Pyridyl)-spiro(cyclopentane-1,3'-benzo[1',2'-b:5',4'-b']dipyrrol)-2'-(1'H, 3'H, 7'H)-one 4 g. (20 mmole) 6'-aminospiro(cyclopentan-1,3'-indoline)-2'-one are introduced into 50 ml. concentrated hydrochloric acid, cooled to 0° C. and 1.5 g. (21.5 mmole) sodium nitrite, dissolved in 5 ml. water, added dropwise thereto. After 15 minutes, 13.5 g. (60 mmole) stannous chloride, dissolved in 10 ml. concentrated hydrochloric acid, are added dropwise thereto at 0° C. After 2 hours at 25° C., 2.2 g. (18 mmole) 4-acetylpyridine are added thereto and the precipitate is filtered off with suction after 3 hours and washed with a little water. As crude product, there are obtained 6.7 g. 4-acetylpyridine-(2'-oxospiro(cyclopentane-1,3'-indoline)-6'-hydrazone hydrochloride, which is further reacted without purification.

6.7 g. of the crude product are slowly introduced, while stirring, into 70 ml. polyphosphoric acid at 120° C. After 2 hours at this temperature, the reaction mixture is poured on to ice, neutralised with aqueous ammonia solution and filtered off with suction. Purification takes place by column chromatography (elution agent: methylene chloride/methanol saturated with ammonia 20:1 v/v). Yield 0.7 g. (11.5% of theory, referred to the amount of amine used); m.p. 326°–329° C., after recrystallisation from ethanol.

EXAMPLE 10

3,3,6-Trimethyl-5-phenylbenzo[1,2-b:5,4-b']dipyrrol-2-(1H, 3H, 7H)-one.

Analogously to Example 5, 4 g. (22.7 mmole) 6-amino-3,3-dimethylindolin-2-one are diazotised and reduced. Subsequently, 3 g. (22.3 mole) phenylacetone are added thereto and the reaction mixture further stirred for 18 hours at 25° C. The oil which separates out is shaken out several times with methylene chloride, evaporated and the residue worked up with cyclohexane and filtered off with suction. The solid residue is again dissolved in methylene chloride, washed twice with aqueous sodium hydrogen carbonate solution and once with water, dried with anhydrous sodium sulphate with the addition of charcoal and crystallised from methylene chloride. Yield 1.25 g. (19% of theory); m.p. 233°–235° C.

Pharmaceutical Activity

Male Sprague-Dawley rats weighing between 350 and 450 g were narcotized by intraperitoneal injection of a barbiturate and fitted with instrumentation for the examinations as follows:

A pressure measuring catheter (Miller Mikrotip TM-/diameter 0.5 mm) was inserted through the arteria carotis dextra into the left ventricle. The pressure inside the left ventricle was continually registered through this catheter. The signal from this Mikrotip was electronically differentiated and (dp/dt)$_{60}$—the slope of the pressure-time curve at a pressure of 60 mmHg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rate were fixed on an electrically heated and thermostated operating table.

Procedure

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained. From the measured data, using a regression calculation, equipotent doses for the positively inotropic effect $\Delta$ $(dp/dt)_{60}$ were calculated. In addition, as criterion for the effectiveness of the substances, the maximum effect obtained maximal increase of $(dp/dt)_{60}$ and its corresponding dose were determined. The table that follows shows the equipotent doses ($DE_{1,5}$=the dose in mg/kg that leads to an increase of $(dp/dt)_{60}$ of 1.5 mHg/sec) and the maximal effectiveness ($W_{max}$=the maximal increase of $(dp/dt)_{60}$.

| Substance from Exp. | $ED_{1,5}$ mHg/sec [mg/kg i.v.] | $W_{max}$ [mHg/sec] | [mg/kg i.v.] |
|---|---|---|---|
| 1. | 0,16 | 3,4 | 3,0 |
| 1.1 | — | >1,0 | >3,0 |
| 1.2 | — | >1,4 | >3,0 |
| 1.3 | — | 0,6 | 0,3 |
| 1.4 | — | >0,3 | >3,0 |
| 2.1 | — | >0,8 | >3,0 |
| 3. | *i.d. tested | +1,5 | |
| 4. | *i.d. tested | +0,9 | |
| 8. | 0,1 | 2,0 | 0,3 |

*intraduodenal dosage of 50 mg/kg.

It will be understood that the specification and examples are illustrative but not limitative of the present invention and that other embodiments within the spirit and scope of the invention will suggest themselves to those skilled in the art.

What is claimed is:

1. A compound of the formula:

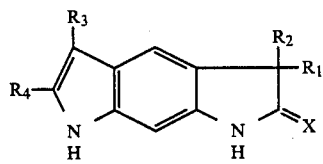

wherein $R_1$ is hydrogen, $C_1$-$C_6$ alkyl, $C_2$-$C_6$ alkenyl, or $C_3$-$C_7$ cycloalkyl;

$R_2$ is hydrogen, $C_1$-$C_6$ alkyl, $C_2$-$C_6$ alkenyl, cyano, or a carbonyl group substituted by hydroxyl, $C_1$-$C_6$ alkyl, $C_1$-$C_6$ alkoxy, amino, $C_1$-$C_6$ alkylamino, di-C]hd 1]l -$C_6$-alkyl-amino or hydrazino; or $R_2$ and $R_1$ together with the carbon to which they are attached form a $C_3$-$C_7$ cycloalkylene ring, or $R_1$ and $R_2$ together form $C_3$-$C_7$ cycloalkylidene, $R_3$ is hydrogen, cyano, $C_1$-$C_7$ alkyl, $C_2$-$C_7$ alkenyl, $C_3$-$C_7$ cycloalkyl, $C_3$-$C_7$ cycloalkenyl, $C_1$-$C_7$ alkylcarbonyl, $C_1$-$C_7$ alkoxycarbonyl, carboxyl, aminocarbonyl, $C_1$-$C_7$ alkylaminocarbonyl, di-$C_1$-$C_7$-alkylaminocarbonyl, or $C_6$-$C_{12}$ aryl;

$R_4$ is hydrogen, $C_1$-$C_7$ alkyl, trihalomethyl, $C_3$-$C_7$ cycloalkyl, hydroxyl, cyano, carboxyl, $C_1$-$C_7$ alkoxy-carbonyl, $C_1$-$C_7$ alkyl-carbonyl, aminocarbonyl, $C_1$-$C_7$ alkyl-aminocarbonyl or di-$C_1$-$C_7$-alkylamino-carbonyl, or $R_4$ is a phenyl ring of the formula:

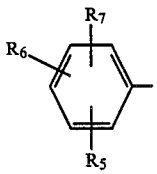

wherein $R_5$, $R_6$ and $R_7$ are the same or different and wherein $R_5$, $R_6$ and $R_7$ each represents hydrogen, $C_1$-$C_5$ alkyl-sulphonyloxy, trifluoromethanesulphonyloxy, $C_1$-$C_5$ alkyl-sulphonylamino, trifluoromethanesulphonylamino, N-$C_1$-$C_5$-alkyl-$C_1$-$C_5$-alkyl-sulphonylamino, N-$C_1$-$C_5$-alkyl-trifluoromethane-sulphonylamino, $C_1$-$C_5$-alkyl-sulphenylmethyl, $C_1$-$C_5$-alkyl-sulphinylmethyl, $C_1$-$C_5$-alkylsulphonymethyl; a carbonyl group substituted by a hydroxyl, $C_1$-$C_5$-alkoxy, amino, $C_1$-$C_5$-alkylamino or di-$C_1$-$C_5$-alkyl-amino; or a sulphonyl group substituted by an amino, $C_1$-$C_5$ alkylamino, di-$C_1$-$C_5$-alkyl-amino or by morpholino, pyrrolidino, piperidino or hexamethyleneiminosulphonyl; or a $C_1$-$C_5$ alkylcarbonylamino, amino-carbonylamino, $C_1C_5$ alkyl-aminocarbonylamino, $C_1$-$C_5$ alkylthio, $C_1$-$C_5$ alkylsulphinyl, $C_1$-$C_5$ alkylsulphonyl, nitro, halogen, amino, hydroxyl, $C_1$-$C_5$-alkyl, $C_1$-$C_5$-alkoxy, $C_2$-$C_5$ alkenyloxy, $C_2$-$C_5$ alkynyloxy, cyano-$C_1$-$C_5$-alkoxy, carboxy-$C_1$-$C_5$-alkoxy, $C_1$-$C_5$-alkoxy-carbonyl-$C_1$-$C_5$-alkoxy, di-$C_1$-$C_5$-alkylamino, 1-imidazolyl, trifluoromethyl or cyano group, X is oxygen or sulphur a tautomer thereof or a physiologically acceptable salt thereof with an inorganic or organic acid.

2. The compound of claim 1 wherein $R_1$ and $R_2$ are the same and are methyl or ethyl or $R_1$ and $R_2$ are different and are selected from the group consisting of hydrogen, methyl, ethyl, isopropyl, cyclopentyl, cyano, acetyl, methoxycarbonyl, ethoxycarbonyl, aminocarbonyl or hydrazinocarbonyl or $R_1$ and $R_2$ together with the carbon atom to which they are attached, form a cycloalkylene ring, $R_3$ is hydrogen, methyl, ethyl, isopropyl, n-butyl, allyl, cyclohexyl, cyclopentenyl, cyano, ethoxycarbonyl or phenyl, $R_4$ is methyl, ethyl, isopropyl, trifluoromethyl, cyclopentyl, hydroxyl, cyano, acetyl, carboxyl, ethoxycarbonyl, aminocarbonyl, methylaminocarbonyl or dimethylaminocarbonyl or $R_4$ is the phenyl radical of general formula (II) in which $R_5$ is hydrogen, methanesulphonyloxy, trifluoromethanesulphonyloxy, methanesulphonylamino, trifluoromethanesulphonylamino, methanesulphonymethylamino, trifluoromethanesulphonylmethylamino, methylsulphenylmethyl, methylsulphinylmethyl, methylsulphonylmethyl, aminocarbonyl, aminosulphonyl, methylaminosulphonyl, dimethylaminosulphonyl, acetylamino, methylthio, methylsulphonyl, hydroxyl, methyl, methoxy, propargyloxy, cyanomethoxy, methoxycarbonylmethoxy, cyano, chloro, nitro, amino, dimethylamino, trifluoromethyl or 1-imidazolyl $R_6$ is hydrogen, methyl, methoxy, dimethylamino or chlorine, $R_7$ is hydrogen or a methoxy and X is oxygen; or a tautomer thereof or a physiologically acceptable salt thereof with an inorganic or organic acid.

3. The compound of claim 1 wherein $R_1$ is methyl or ethyl, $R_2$ is hydrogen, methyl or ethyl or together with $R_1$ is a cyclopentyl ring, $R_3$ is hydrogen, methyl, ethyl or phenyl, $R_4$ is methyl, ethyl, hydroxyl, carboxyl, ethoxycarbonyl, aminocarbonyl or a phenyl unsubstituted or substituted by hydroxyl, methoxy, cyano, chlorine, methyl or 1-imidazolyl and X is oxygen; or a tautomer thereof or a physiologically acceptable salt thereof with an inorganic or organic acid.

4. The compound of claim 2 wherein $R_4$ is methyl, ethyl, isopropyl, trifluoromethyl, cyclopentyl, hydroxyl, cyano, acetyl, carboxyl, ethoxycarbonyl, aminocarbonyl, methylaminocarbonyl or dimethylaminocarbonyl.

5. The compound of claim 2 wherein $R_4$ is said phenyl ring of formula (II).

6. The compound of claim 1 wherein $R_1$ and $R_2$ are the same and are methyl or ethyl or $R_1$ and $R_2$ are different and are hydrogen, methyl or ethyl or $R_1$ and $R_2$ together form a cyclopentyl ring.

7. The compound of claim 1 designated 3,3-dimethyl-6-[4-(1H-imidazol-1-yl)-phenyl]-benzo [1,2-b:5,4-b']dipyrrol-2-(1H, 3H, 7H)-one.

8. The compound of claim 1 designated 3,3,6-trimethylbenzo[1,2-b:5,4-b']dipyrrol-2-(1H, 3H, 7H)-one.

9. The compound of claim 1 designated 3,3-dimethyl-6-phenylbenzo[1,2-b:5,4-b']dipyrrol-2-(1H, 3H, 7H)-one.

10. The compound of claim 1 designated 3,3-dimethylbenzo-1,2-b:5.4-b']dipyrrol-2,6-(1H, 3H, 5H, 7H)-dione.

11. A pharmaceutical composition for the treatment of heart and ciculatory diseases comprising an effective amount of the compound of claim 1 in a pharmaceutically acceptable carrier.

12. The pharmaceutical composition of claim 11 wherein said compound is
3,3-dimethyl-6-[4-(1H-imidazol-1-yl)-phenyl]-benzo [1,2-b:5,4-b']dipyrrol-2-(1H, 3H, 7H)-one;
3,3-dimethylbenzo[1,2-b:5,4-b']dipyrrol-2,6-(1H, 3H, 5H, 7H)-dione;
3,3,6-trimethylbenzo[1,2-b:5,4-b']dipyrrol-2-(1H, 3H, 7H)-one;
3,3-dimethyl-6-phenylbenzo[1,2-b:5,4-b']dipyrrol-2-(1H, 3H, 7H)-one.

13. A method of treating heart or circulatory diseases in a patient having the disease comprising administering an effective amount for treating heart or circulatory diseases, of the compound of claim 1.

14. The method of claim 13 wherein 0.1 to 500 mg per kg body weight, are administered per day.

15. The method of claim 14 wherein 5 to 500 mg are administered.

16. A method of treating heart or circulatory diseases in a patient having the disease comprising administering an effective amount for treating heart or circulatory diseases, of the composition of claim 12.

* * * * *

UNITED STATES PATENT AND TRADEMARK OFFICE
CERTIFICATE OF CORRECTION

PATENT NO. : 4,874,756

DATED : October 17, 1989

INVENTOR(S) : Alfred Mertens et al

It is certified that error appears in the above-identified patent and that said Letters Patent is hereby corrected as shown below:

Column 3, line 3, change "cyclopentyl" to --cyclopentenyl--.

Column 3, line 19, change "cyclopentyl" (second occurrence) to --cyclopentenyl--.

Column 5, line 16, change "cyclopentyl" to --cyclopentenyl--.

Column 8, line 64, change "syndnones" to --sydnones--.

Column 9, line 7, change "syndnones" to --sydnones--.

Column 12, line 54, change "sere" to --serve--.

Column 14, line 67, change "[12-b:5,4-b']" to --[1,2-b:5,4-b']--.

Column 15, line 21, after "benzo" change "-" to --[--.

UNITED STATES PATENT AND TRADEMARK OFFICE
CERTIFICATE OF CORRECTION

PATENT NO. : 4,874,756
DATED : October 17, 1989
INVENTOR(S) : Alfred Mertens et al It is certified that error appears in the above-identified patent and that said Letters Patent is hereby corrected as shown below:

Column 15, line 29, after "cyclopentan-" change "2,3" to --1,3'--.

Column 21, line 52, change "di-C]hd1]1-$C_6$" to --di-$C_1$-$C_6$--.

Column 24, line 2 (Claim 10), after "thylbenzo" change "-" to --[--.

Signed and Sealed this

Eighth Day of January, 199

Attest:

HARRY F. MANBECK, JR.

*Attesting Officer*     Commissioner of Patents and Trademarks